US 9,339,193 B2

(12) United States Patent
Cilibrasi et al.

(10) Patent No.: US 9,339,193 B2
(45) Date of Patent: May 17, 2016

(54) PHYSIOLOGICAL ADAPTABILITY SYSTEM WITH MULTIPLE SENSORS

(75) Inventors: Rudi Cilibrasi, Sunnyvale, CA (US); David L. Marvit, San Francisco, CA (US)

(73) Assignee: FUJITSU LIMITED, Kawasaki (JP)

( * ) Notice: Subject to any disclaimer, the term of this patent is extended or adjusted under 35 U.S.C. 154(b) by 1032 days.

(21) Appl. No.: 13/476,885

(22) Filed: May 21, 2012

(65) Prior Publication Data

US 2013/0310654 A1    Nov. 21, 2013

(51) Int. Cl.
| A61B 5/00 | (2006.01) |
| G06F 19/00 | (2011.01) |
| A61B 5/0205 | (2006.01) |
| A61B 5/0456 | (2006.01) |
| A61B 5/024 | (2006.01) |
| A61B 5/08 | (2006.01) |

(52) U.S. Cl.
CPC ............... *A61B 5/0205* (2013.01); *A61B 5/024* (2013.01); *A61B 5/0456* (2013.01); *A61B 5/08* (2013.01); *A61B 5/0816* (2013.01); *A61B 5/4035* (2013.01); *A61B 5/72* (2013.01); *G06F 19/30* (2013.01); *G06F 19/34* (2013.01)

(58) Field of Classification Search
CPC .... A61B 5/0002; A61B 5/0205; A61B 5/024; A61B 5/0456; A61B 5/08–5/082; A61B 5/165; A61B 5/4076; A61B 5/72; G06F 19/34–19/3418
See application file for complete search history.

(56) References Cited

U.S. PATENT DOCUMENTS

| 6,305,943 | B1 * | 10/2001 | Pougatchev | ........... | A61B 5/486 |
| | | | | | 434/238 |
| 7,117,032 | B2 | 10/2006 | Childre et al. | | |
| 7,163,512 | B1 | 1/2007 | Childre et al. | | |
| 8,123,696 | B2 | 2/2012 | Childre et al. | | |
| 2004/0127804 | A1 * | 7/2004 | Hatlesad | .............. | A61B 5/0205 |
| | | | | | 600/513 |
| 2004/0236236 | A1 * | 11/2004 | Yanagidaira | ............. | A61B 5/18 |
| | | | | | 600/509 |
| 2005/0187426 | A1 * | 8/2005 | Elliott | .................... | A61B 5/486 |
| | | | | | 600/26 |
| 2005/0288601 | A1 * | 12/2005 | Wood et al. | ................... | 600/513 |
| 2007/0299354 | A1 | 12/2007 | Striepe et al. | | |

(Continued)

FOREIGN PATENT DOCUMENTS

| WO | 90/03144 A1 | 4/1990 |
| WO | 2009/104127 A1 | 8/2009 |

(Continued)

OTHER PUBLICATIONS

Butler, E. et al; "Respiratory sinus arrhythmia, emotion, and emotion regulation during social interaction"; Psychophysiology, 43 (2006), 612-622.*

(Continued)

*Primary Examiner* — William Thomson
*Assistant Examiner* — Marie Archer
(74) *Attorney, Agent, or Firm* — Maschoff Brennan

(57) ABSTRACT

According to an aspect of an embodiment, a method of measuring physiological adaptability of a subject is described. The method may include receiving, from a first sensor, a first data signal indicating a first biological function of the subject. The method may also include receiving, from a second sensor, a second data signal indicating a second biological function of the subject. The method may also include calculating an adaptability of the subject based on the first data signal and the second data signal. The method may also include reporting the calculated adaptability.

17 Claims, 5 Drawing Sheets

(56) References Cited

U.S. PATENT DOCUMENTS

| | | | |
|---|---|---|---|
| 2008/0214903 A1* | 9/2008 | Orbach | 600/301 |
| 2010/0041967 A1 | 2/2010 | McCraty et al. | |
| 2010/0179438 A1* | 7/2010 | Heneghan et al. | 600/484 |
| 2011/0295138 A1* | 12/2011 | Lai et al. | 600/529 |
| 2015/0150514 A1* | 6/2015 | Batchinsky | A61B 5/7275 600/301 |

FOREIGN PATENT DOCUMENTS

| | | |
|---|---|---|
| WO | 2009/136341 A2 | 11/2009 |
| WO | 2009/138923 A1 | 11/2009 |

OTHER PUBLICATIONS

Porges, S. W.: "Cardiac Vagal Tone: A physiological Index of Stress"; Neuroscience and Biobehavioral Reviews; vol. 19; No. 2 (1995) pp. 225-233.*

Grossman, P et al; "A Comparison of Three Quantification Methods for Estimation of Respiratory Sinus Arrhythmia" Psychophysiology, vol. 27, No. 6 (1990) pp. 702-714.* deGeus, E. J. C et al; "Ambulatory measurement of respiratory sinus arrhythmia and respiration rate"; Biological Psychology 41 (1995) 205-227.*

Etzel, Joset Amy, "Algorithms and procedures to analyze physiological signals in psychophysiological research" (2006). Retrospective Theses and Dissertations. Paper 1255. pp. 1-177.*

Grossman, P. et al; "Toward understanding respiratory sinus arrhythmia: Relations to cardiac vagal tone, evolution and biobehavioral functions"; Biological Psychology 74 (2007) 263-285.*

Kurt Plarre et al: "Continuous inference of psychological stress from sensory measurements collected in the natural environment". Information Processing in Sensor Networks (IPSN), 2011 10th International Conference on, IEEE, Apr. 12, 2011, pp. 97-108.

Grimaldi D et al: "Spectral analysis of heart rate variability reveals an enhanced sympathetic activity in narcolepsy with cataplexy", Clinical Neurophysiology, Elsevier Science, IE, vol. 121, No. 7, Jul. 1, 2010 pp. 1142-1147.

Seung-Hun Park et al: "A Biofeedback-Based Breathing Induction System", Bioinformatics and Biomedical Engineering, 2009. ICBBE 2009. 3rd International Conference on, IEEE, Piscataway, NJ, USA Jun. 11, 2009, pp. 1-4.

European Search Report dated Aug. 29, 2013 in application No. 13167818.7.

* cited by examiner

PHYSIOLOGICAL ADAPTABILITY SYSTEM WITH MULTIPLE SENSORS

FIELD

The embodiments discussed herein are related to determining physiological adaptability of a subject.

BACKGROUND

Reduced parasympathetic activity may be found in individuals under mental or emotional stress, suffering from panic, anxiety or worry, depression, high blood pressure, heart disease and many other disorders.

Some devices, such as those developed by the Institute of Heart Math in Boulder Creek, Calif., have been developed to aid users in identifying and/or improving parasympathetic activity. Such devices may produce simple metrics associated with a meditation state, or entrainment, in which the heart rate varies with the breath as measured by heart rate alone. These and similar devices typically provide metrics based on measurements from a single sensor, such as a heart rate monitor. Additionally, these and similar devices may be limited to use in controlled environments and/or may not tolerate noise arising from a subject undertaking everyday activities while using such devices.

The subject matter claimed herein is not limited to embodiments that solve any disadvantages or that operate only in environments such as those described above. Rather, this background is only provided to illustrate one example technology area where some embodiments described herein may be practiced.

SUMMARY

According to an aspect of an embodiment, a method of measuring physiological adaptability of a subject is described. The method may include receiving, from a first sensor, a first data signal indicating a first biological function of the subject. The method may also include receiving, from a second sensor, a second data signal indicating a second biological function of the subject. The method may also include calculating an adaptability of the subject based on the first data signal and the second data signal. The method may also include reporting the calculated adaptability.

The object and advantages of the embodiments will be realized and achieved at least by the elements, features, and combinations particularly pointed out in the claims.

It is to be understood that both the foregoing general description and the following detailed description are exemplary and explanatory and are not restrictive of the invention, as claimed.

BRIEF DESCRIPTION OF THE DRAWINGS

Example embodiments will be described and explained with additional specificity and detail through the use of the accompanying drawings in which.

DESCRIPTION OF EMBODIMENTS

Embodiments of the present invention will be explained with reference to the accompanying drawings.

Figure 1:
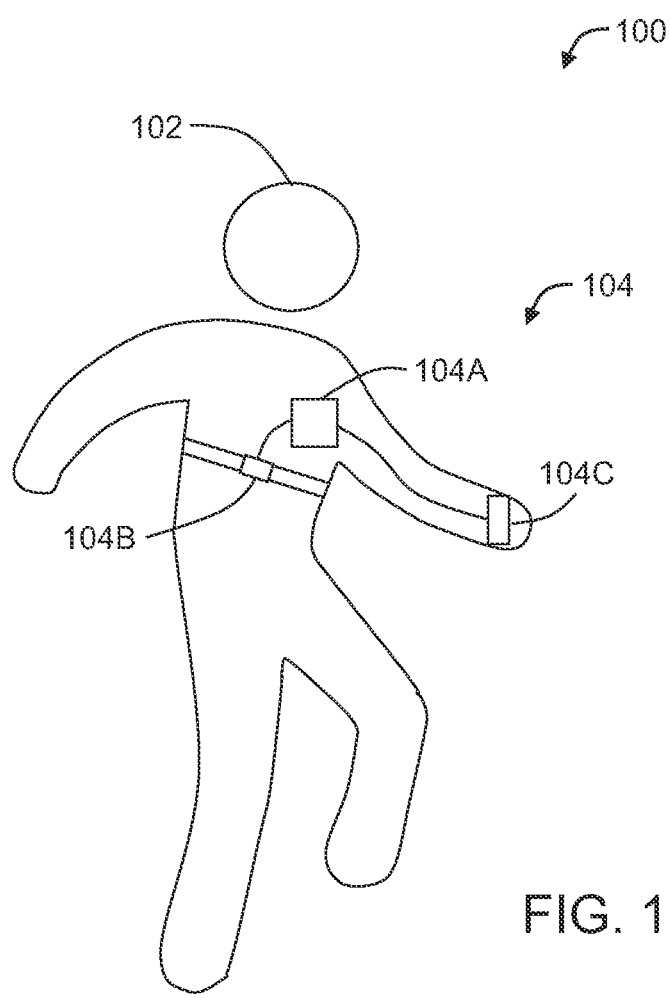
FIG. 1 illustrates an example environment 100 in which some embodiments described herein may be implemented.

FIG. 1 illustrates an example environment 100 in which some embodiments described herein may be implemented. The environment includes a subject 102 and a system 104 for measuring a physiological adaptability of the subject 102.

The environment 100 may include an uncontrolled environment. As used herein, an uncontrolled environment may include any environment in which activities in which the subject 102 may participate while being tested by the system 104 are not controlled or substantially limited. Moreover, the system 104 may be a mobile system such that the subject 102 may participate in virtually any desired activity while being tested by the system 104. For example, the subject 102 is illustrated as walking in the example of FIG. 1, and other activities in which the subject 102 may participate while using the system 104 may include, but are not limited to, other types of exercise, working, driving, relaxing, meditating, eating, sleeping, or the like or any combination thereof. The ability to use the system 104 in uncontrolled environments and the mobile nature of the system 104 may allow the subject 102 to use the system 104, at least in some embodiments, while moving around, while at work or play or doing virtually any desired activity without having to limit the activities in which the subject 102 participates during the testing and/or without having to go to a particular location to be tested.

In contrast, some systems and devices for testing subjects are limited to use in controlled environments. Examples of such systems and devices may include blood pressure devices, weight scales, certain respiratory testing devices, and so on. As used herein, a controlled environment may include any environment in which activities in which the subject 102 may participate while being tested by the system 104 are controlled or limited. The activities may be limited during testing to substantially prevent or minimize noise that might otherwise be introduced into corresponding measurements. While the system 104 has been described as being used in uncontrolled environments, the system 104 may optionally be used in controlled environments as well.

In the illustrated embodiment, the system 104 includes a computing device 104A and first and second sensors 104B, 104C. Although two sensors 104B, 104C are illustrated in FIG. 1, the system 104 may optionally include more than two sensors 104B, 104C. Each of the sensors 104B, 104C may be communicatively coupled to the computing device 104A and may be configured to generate a data signal indicating a corresponding biological function of the subject 102, the corresponding data signal being received by the computing device 104A.

The respective biological function measured by the corresponding first or second sensor 104A, 104B may include, but is not limited to, a respiratory function, a dermal function, a motor function, a cardiac function, a biochemical function, or the like or any combination thereof. Specific examples of some of the foregoing include, but are not limited to, breathing rate, breathing level, skin temperature, exercise or other motor functions performed by the subject 102, heart rate, or blood-sugar level. The given function may be measured by direct measurement or by measuring a proxy for the given function. For instance, breathing may be directly measured by directly measuring the amount of air inhaled and exhaled by the subject 102, or may be indirectly measured by measuring a proxy for breathing such as chest circumference.

One or more of the respective biological functions measured by each of the first and second sensors 104B, 104C may vary over time. For example, breathing may vary in a substantially periodic fashion with generally alternating periods of inhaling versus exhaling. As another example, skin temperature may vary over time as a function of ambient temperature and/or other factors.

For convenience in the discussion that follows, the biological function measured by the first sensor 104B and the biological function measured by the second sensor 104B may be respectively referred to as the first and second biological functions. In some embodiments, a variability of the second biological function may depend on a variability of the first biological function. For example, cardiac function may depend on respiratory function such that heart rate may increase while inhaling and may decrease while exhaling. As another example, cardiac function may depend on dermal function such that heart rate may increase with increasing skin temperature and decrease with decreasing skin temperature. As yet another example, respiratory function may depend on motor function such that breathing rate may increase with increasing exercise intensity and decrease with decreasing exercise intensity. As still another example, biochemical function may depend on motor function such that blood-sugar level may vary with physical activity level. The foregoing are provided by way of example only and are not intended to be limiting.

In general, some embodiments described herein may combine the measurements generated by the first and second sensors 104B, 104C, or more specifically, the corresponding data signals generated by the first and second sensors 104B, 104C, into a single metric or constant number as described in more detail below. The metric may be representative of a physiological adaptability of the subject 102. For example, data signals indicating cardiac function and respiratory function may be combined into a metric representative of a stress adaptability of the subject 102. As another example, data signals indicating cardiac function and dermal function may be combined into a metric representative of a temperature adaptability of the subject 102. As yet another example, data signals indicating respiratory function and motor function may be combined into a metric representative of a respiratory adaptability of the subject 102. As still another example, data signals indicating biochemical function and motor function may be combined into a metric representative of a sugar metabolization adaptability of the subject 102. The foregoing are provided by way of example only and are not intended to be limiting.

More generally, data signals representing at least two different biological functions where one of the biological functions at least partially depends on the other may be combined to generate a metric indicating a corresponding adaptability of the subject 102. For convenience in the discussion that follows, however, embodiments will be described in which one of the data signals may indicate a respiratory function—such as breathing—of the subject 102, the other of the data signals may indicate a cardiac function—such as heart rate—of the subject 102, and the metric calculated by combining the two data signals may represent a stress adaptability—such as a respiratory sinus arrhythmia (RSA)—of the subject 102. In these and other embodiments, the first sensor 104B may include a respiratory sensor and the second sensor 104C may include a cardiac sensor. Some non-limiting examples of respiratory sensors include chest circumference sensors, respiratory inductance plethysmographs (RIPs), and blood oxygen level sensors. Some non-limiting examples of cardiac sensors include heart rate monitors attachable to the chest, finger, or other areas of the subject 102, electrocardiography (ECG or EKG) devices, and Holter monitors.

Figure 2:
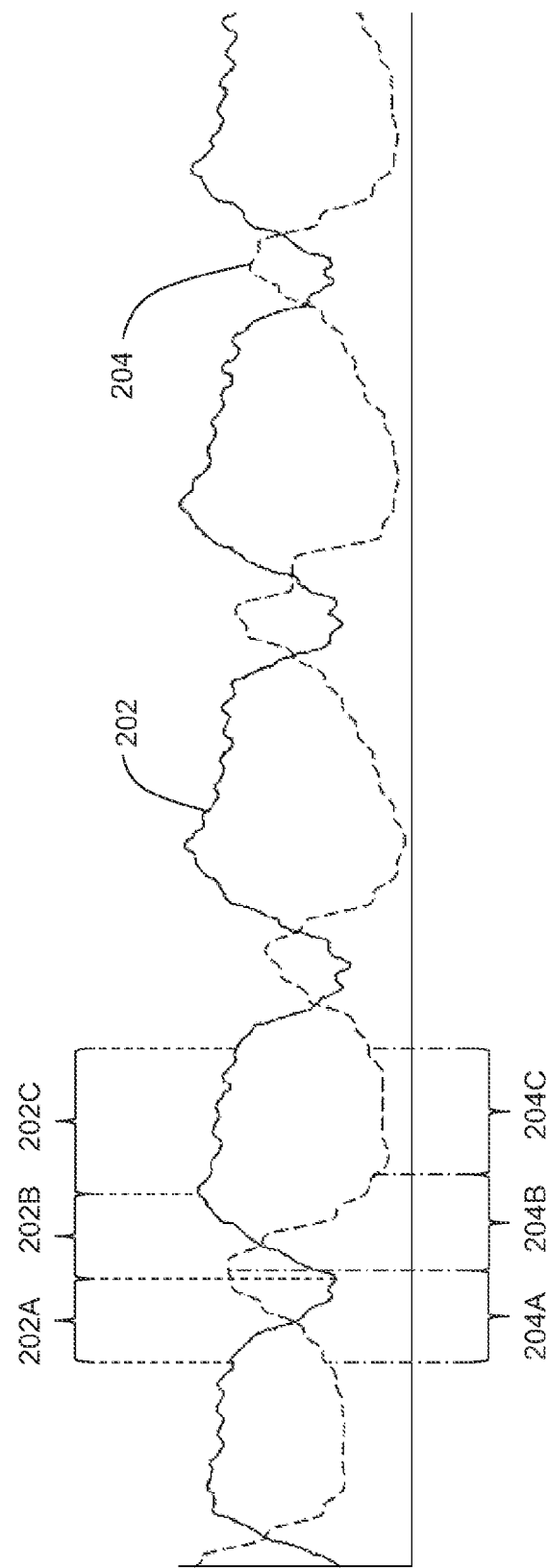
FIG. 2 is an example graph of breathing level and heart rate over time for a subject.

FIG. 2 is an example graph of breathing level and heart rate over time for a subject, such as the subject 102 of FIG. 1. More particularly, FIG. 2 includes a first data signal 202 representing breathing level of the subject and a second data signal 204 representing heart rate of the subject. Moreover, the first and second data signals 202, 204 have been time synchronized in FIG. 2.

The first data signal 202 representing breathing level includes negative slope portions and positive slope portions. Negative slope portions of the first data signal 202, such as a portion 202A, represent the subject inhaling. Positive slope portions of the first data signal 202, such as a portion 202B, represent the subject exhaling. The first data signal 202 may additionally include relatively flat portions, such as a relatively flat portion 202C, where it is not entirely clear whether the subject is inhaling or exhaling.

The second data signal 204 representing heart rate includes positive slope portions and negative slope portions. Positive slope portions of the second data signal 204, such as a positive slope portion 204A, represent the subject's heart rate increasing. Negative slope portions of the second data signal 204, such as a negative slope portion 204B, represent the subject's heart rate decreasing. The second data signal 204 may additionally include relatively flat portions, such as a relatively flat portion 204C, where it is not entirely clear whether the subject's heart rate is increasing or decreasing.

As illustrated in FIG. 2, the subject's heart rate periodically varies over time as a function of the breathing. The variation in heart rate that occurs during each breathing cycle as illustrated in FIG. 2 may be referred to as RSA.

In more detail, the subject's heart rate may generally increase while the subject inhales and may generally decrease while the subject exhales. According to some embodiments described herein, a measurement of a difference between an average heart rate during inhaling and an average heart rate during exhaling may be calculated as a single metric representing a stress adaptability of the subject.

The stress adaptability calculated across a population of subjects may vary along a spectrum. Stress adaptability at one end of the spectrum may be as low as zero in some embodiments. For instance, subjects with pacemakers that regulate the subjects' respective heart rate at a corresponding constant rate may not exhibit any RSA. The breathing cycle of these and other subjects may create stress on the subjects' bodies and the ability of a healthy heart to increase or decrease its rate may accommodate such stress. Because the heart rate of a subject with a pacemaker is at a constant rate such that the heart rate may be unable to adjust to varying conditions, such a subject may be relatively less able to adapt to stress as reflected by a stress adaptability of zero. In contrast, subjects with heart rates that exhibit a relatively greater change during their breathing cycles may be relatively better able to adapt to stress, which may be reflected by a relatively higher stress adaptability as calculated herein.

Stress adaptability may be used by healthcare workers such as doctors or nurses and/or by subjects for diagnostic or pre-diagnostic purposes, or the like. Alternately or additionally, subjects with relatively low stress adaptability may be prescribed medications or routines to improve their stress adaptability and stress fitness. Such routines may include exercise, meditation, time off work, vacation, or the like or any combination thereof.

Figure 3A:
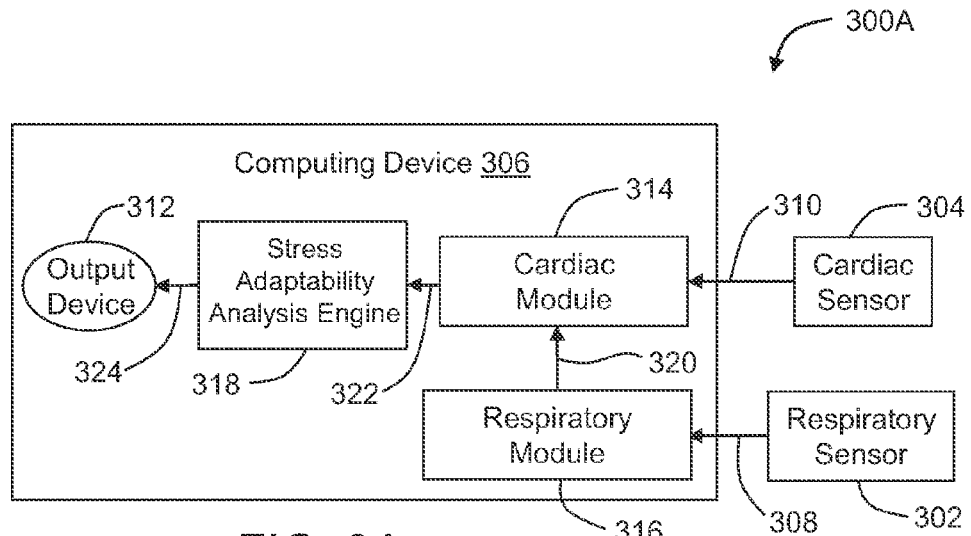
FIG. 3A is a block diagram of an example system for measuring stress adaptability of a subject.

FIG. 3A is a block diagram of an example system 300A for measuring stress adaptability of a subject, such as the subject 102 of FIG. 1. The system 300A may correspond to the system 104 of FIG. 1 for example. Although described in the context of measuring stress adaptability, embodiments of the system 300A or variations thereof may instead be applied for measuring some other physiological adaptability of the subject.

The system 300A may include a respiratory sensor 302, a cardiac sensor 304, and a computing device 306. The respiratory sensor 302 may be configured to generate a first data signal 308 indicating respiratory function of a subject. The cardiac sensor 304 may be configured to generate a second data signal 310 indicating cardiac function of the subject.

The computing device 306 may be communicatively coupled to the respiratory sensor 302 and the cardiac sensor 304 via a wired or wireless connection. The computing device 306 may be configured to receive the first data signal 308 and the second data signal 310. The computing device 306 may additionally be configured to calculate a stress adaptability of the subject based on the first data signal 308 and the second data signal 310. The computing device 306 may additionally be configured to report the calculated stress adaptability to a user via an output device 312. The output device 312 may be included as part of the computing device 306 or the output device 312 may be provided separately from the computing device 306. The user to whom the calculated stress adaptability is reported may include the subject, a healthcare worker, or any other user.

The computing device 306 may include a cardiac module 314, a respiratory module 316, a stress adaptability analysis engine 318 and the output device 312. The cardiac module 314, the respiratory module 316 and the stress adaptability analysis engine 318 may be implemented in software, hardware, or a combination thereof. When implemented at least partially in software, the computing device 306 may additionally include a memory and a processing device configured to execute computer instructions stored in the memory to cause the computing device 306 to perform the operations described herein, such as operations described with respect to the cardiac module 314, the respiratory module 316 and the stress adaptability analysis engine 318. Although not shown, the computing device 306 may optionally include a battery configured to power the system 300A such that the system 300A may be mobile.

The respiratory module 316 may be configured to determine time intervals when the subject is generally inhaling and time intervals when the subject is generally exhaling. The respiratory module 316 may output a control signal 320 to the cardiac module 314 indicating the time intervals when the subject is generally inhaling and the time intervals when the subject is generally exhaling.

The cardiac module 314 may be configured to receive the control signal 320. Based on the control signal 320, the cardiac module 314 may be configured to collect heart beat and time interval data associated with time intervals when the subject is generally inhaling and time intervals when the subject is generally exhaling. A data signal 322 representing the collected heart beat and time interval data may be output to the stress adaptability analysis engine 318.

The stress adaptability analysis engine 318 may be configured to receive the data signal 322. Based on the data signal 322, the stress adaptability analysis engine 318 may be configured to determine a first average heart rate corresponding to time intervals when the subject is generally inhaling and a second average heart rate corresponding to time intervals when the subject is generally exhaling. The stress adaptability analysis engine 318 may be further configured to calculate a difference between the first average heart rate and the second average heart rate as the calculated stress adaptability. The stress adaptability analysis engine 318 may output a result signal 324 to the output device 312 indicating the calculated stress adaptability.

The output device 312 may include a display device, such as a touchscreen display or non-touchscreen display, a speaker, or other suitable output device. The output device 312 may be configured to receive the result signal 324 and to report the calculated stress adaptability indicated by the result signal 324 by, e.g., outputting the calculated stress adaptability.

Figure 3B:
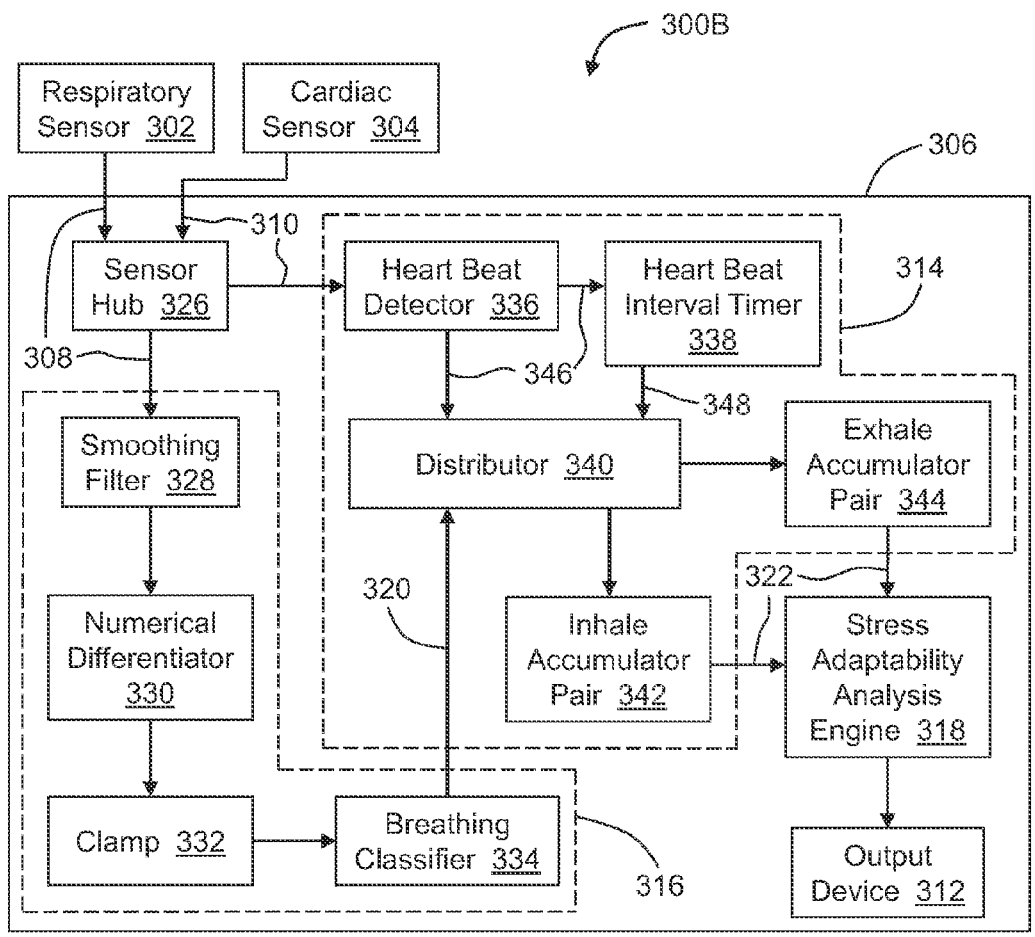
FIG. 3B is a block diagram of an embodiment of the system of FIG. 3A.

FIG. 3B is a block diagram of an embodiment of the system 300A of FIG. 3A, referred to herein as the system 300B. As illustrated, the system 300B of FIG. 3B includes the respiratory sensor 302, the cardiac sensor 304, and the computing device 306. The computing device 306 includes the output device 312, the cardiac module 314, the respiratory module 316 and the stress adaptability analysis engine 318. The computing device 306 may additionally include a sensor hub 326.

The sensor hub 326 may be communicatively coupled to the respiratory sensor 302 and the cardiac sensor 304. The sensor hub 326 may be configured to receive and temporally synchronize the first data signal 308 received from the respiratory sensor 302 and the second data signal 310 received from the cardiac sensor 304. In these and other embodiments, the sensor hub 326 may be configured to measure time in hours, minutes, and/or seconds to a predetermined precision. For example, the sensor hub 326 may be configured to measure time in seconds to a precision of at least 0.1 second.

The respiratory module 316 may be communicatively coupled to the sensor hub 326. The cardiac module 314 may be communicatively coupled to the sensor hub 326 and the respiratory module 316. The stress adaptability analysis engine 318 may be communicatively coupled to the cardiac module 314. The output device 312 may be communicatively coupled to the stress adaptability analysis engine 318.

The respiratory module 316 may include a smoothing filter 328, a numerical differentiator 330 communicatively coupled to the smoothing filter 328, a clamp 332 communicatively coupled to the numerical differentiator 330, and a breathing classifier 334 communicatively coupled to the clamp 332.

The cardiac module 314 may include a heart beat detector 336, a heart beat interval timer 338 communicatively coupled to the heart beat detector 336, a distributor 340 communicatively coupled to the heart beat detector 336 and the heart beat interval timer 338, an inhale accumulator pair 342 communicatively coupled to the distributor 340, and an exhale accumulator pair 344 communicatively coupled to the distributor 340.

An embodiment of an algorithm that may be implemented by the computing device 306 to calculate stress adaptability of the subject will now be described. However, the described embodiment is not intended to be limiting and other embodiments and/or algorithms may be implemented to calculate stress adaptability or other physiological adaptability of the subject.

The first data signal 308 generated by the respiratory sensor 302 may include a series of instantaneous measurements of respiratory function of the subject at a predetermined frequency and/or precision. For example, the first data signal 308 may include instantaneous measurements of blood oxygen level at a frequency of at least 5 Hz and a precision of at least 6 bits. The measurements may be in the form of a time series that may be represented as a linear interpolation S(t) of the time series.

A temporal window of length $T_w$ may be defined. In some embodiments, $T_w$ may be about 1000 seconds. Over a range from $t-T_w$ to $t$, S(t) may have a maximum value $S_{max}(t)$ and a minimum value $S_{min}(t)$. A difference $S_{ds}(t)$ may be calculated according to Equation 1:

$$S_{ds}(t)=S_{max}(t)-(t) \quad \text{Eq. 1.}$$

Equation 1 may represent a calculation of a sliding window range bound to find a bound over time of the breathing level represented by S(t).

A threshold value $S_{de}(t)$ may be calculated according to Equation 2:

$$S_{de}(t)=S_{ds}(t)/C_1 \quad \text{Eq. 2,}$$

where $C_1$ is a constant. The constant $C_1$ may be selected based on an estimated average number of breaths or breathing cycles per time period for a subject such that the threshold value $S_{de}(t)$ may represent a very rough estimate of a usual change in respiratory function such as oxygen level, chest circumference, or the like, between two successive heart beats. For example, where an estimated average number of breathing cycles is six per minute, the constant $C_1$ may be the number ten, which may correspond to an average number of heart beats per breathing cycle.

In some embodiments, the constant $C_1$ may be set to a number lower than an average number of heart beats per breathing cycle, such as five in this example, to avoid excessive "clipping". In these and other embodiments, heart beats occurring where the subject is inhaling or exhaling twice (or some other multiple) as fast as average or faster may count double (or some other multiple). Such an amount of clipping may allow for reasonably clean data filtering.

A first inhale function, $I(t_a, t_b)$, may be calculated according to Equation 3:

$$I(t_a,t_b)=[S(t_b)-S(t_a)]/S_{de}(t_b) \quad \text{Eq. 3,}$$

where $S(t_b)$ is the value of S(t) at time $t_b$ corresponding to an instantaneous measurement of the respiratory function at time $t_b$, $S(t_a)$ is the value of S(t) at time $t_a$ corresponding to an instantaneous measurement of the respiratory function at time $t_a$, $t_b$ occurs after $t_a$, $t_a$ and $t_b$ coincide with a sequential pair of detected heart beats, and $S_{de}(t_b)$ is the value of $S_{de}(t)$ for the temporal window $T_w$ in a range from $t_b-T_w$ to $t_b$.

A second inhale function, $I_c(t_a, t_b)$, may be calculated according to Equation 4:

$$I_c(t_a,t_b)=I(t_a,t_b), \text{ clamped to the range } -1 \leq I_c(t_a,t_b) \leq 1 \quad \text{Eq. 4.}$$

A third inhale function, $I_n(t_a, t_b)$, may be calculated according to Equation 5:

$$I_n(t_a,t_b)=[I_c(t_a,t_b)+1]/2 \quad \text{Eq. 5.}$$

The three inhale functions of Equations 3-5 may generally indicate how much inhaling or exhaling occurs in between successive heart beats detected at times $t_a$ and $t_b$. The third inhale function $I_n(t_a, t_b)$ may vary in a range from $0 \leq I_n(t_a, t_b) \leq 1$ because of clamping and may serve as a way to categorize each heart-beat interval $t_a$ to $t_b$ as during an inhale, during an exhale, or somewhere in between. For example, when the third inhale function $I_n(t_a, t_b)$ is 1 or 0, the associated heart-beat interval may be categorized as respectively occurring during an inhale or an exhale. When the third inhale function $I_n(t_a, t_b)$ is less than one and greater than 0, the associated heart-beat interval may be categorized as somewhere in between an inhale or an exhale.

For each detected heart beat occurring at time $t_n$, a time interval, D(n), may be calculated according to Equation 6:

$$D(n)=t_n-t_{n-1} \quad \text{Eq. 6,}$$

where D(n) represents a length of a time interval from one heart beat to the next. A heart rate approximation for each heart beat may be computed by accumulating D(n) in a time accumulator $A_d$ and adding B=1 for each beat in a beat accumulator $A_b$.

The average heart rate P(t) may be calculated according to Equation 7:

$$P(t)=[A_b*C_2]/A_d \quad \text{Eq. 7,}$$

where $C_2$ is a constant. The constant $C_2$ may be selected as a conversion factor to obtain a desired set of units for the average heart rate. Where time and/or time intervals are measured in seconds as described in some embodiments herein, the constant $C_2$ may be selected as the number one if units of beats per second for the heart rate P(t) are desired, or as the number sixty if units of beats per minute for the heart rate P(t) are desired, or as some other suitable value as desired.

Alternately, two different sets of accumulators may be used to calculate both an inhale average heart rate, $P_i(t)$, and an exhale average heart rate, $P_e(t)$. The set of accumulators associated with $P_i(t)$ may include a time accumulator $A_{id}$ and a beat accumulator $A_{ib}$. Similarly, the set of accumulators associated with $P_e(t)$ may include a time accumulator $A_{ed}$ and a beat accumulator $A_{eb}$.

The quantities D(n) and B may be distributed across both sets of accumulators weighted by the third inhale function $I_n(t_a, t_b)$ such that on each cycle, the entire quantities D(n) and B may be provided to a corresponding accumulator in whole for $I_n(t_a, t_b)=1$ or 0, or in part for $0<I_n(t_a, t_b)<1$. More particularly, if $I_n(t_a, t_b)=1$, the entire D(n) and B=1 may be respectively provided to the inhale time and beat accumulators $A_{id}$ and $A_{ib}$. Alternately, if $I_n(t_a, t_b)=0$, the entire D(n) and B=1 may be respectively provided to the exhale time and beat accumulators $A_{ed}$ and $A_{eb}$. Alternately, if $0<I_n(t_a, t_b)<1$, the time interval D(n) may be determined to be a split time interval in which a first portion $p_1=I_n(t_a, t_b)$ of each of D(n) and B=1 may be respectively provided to the inhale time and beat accumulators $A_{id}$ and $A_{ib}$ and a second portion $p_2=1-p_1$ of each of D(n) and B=1 may be respectively provided to the exhale time and beat accumulators $A_{ed}$ and $A_{eb}$, or the portion provided to each set of accumulators for split time intervals may be determined according to some other algorithm.

In view of the foregoing, the inhale average heart rate, $P_i(t)$, and the exhale average heart rate, $P_e(t)$, may be calculated according to Equations 8 and 9, respectively:

$$P_i(t)=[A_{ib}*C_2]/A_{id} \quad \text{Eq. 8, and}$$

$$P_e(t)=[A_{eb}*C_2]/A_{ed} \quad \text{Eq. 9.}$$

Finally, stress adaptability V(t) may be modeled according to Equation 10 as a difference between heart rate during inhales and heart rate during exhales:

$$V(t)=P_i(t)-P_e(t) \quad \text{Eq. 10.}$$

With combined reference to FIGS. 3A-3B and equations 1-10 and the associated description, the sensor hub 326 may receive the first data signal 308 from the respiratory sensor 302 and the second data signal 310 from the cardiac sensor 304 and may temporally synchronize the first data signal 308 and the second data signal 310. The sensor hub 326 may additionally calculate the difference $S_{ds}(t)$ and/or the threshold value $S_{de}(t)$. The various components of the computing device 306 may communicate calculated values, parameters and/or data signals to subsequent components as desired so that the subsequent components may perform corresponding functions as described herein. Moreover, while specific components may be described as performing specific calculations or other operations, in other embodiments other components than those described may perform the specific calculations or other operations.

The smoothing filter 328 may digitally filter the first data signal 308 to smooth the first data signal 308 before providing it to the numerical differentiator 330.

The numerical differentiator 330 may calculate the first inhale function $I(t_a, t_b)$ from measurements $S(t_b)$, $S(t_a)$ included in or interpolated from the digitally filtered first data signal received from the smoothing filter 328 and from $S_{de}(t_b)$ calculated by the sensor hub 326.

The clamp 332 may calculate the second inhale function $I_c(t_a, t_b)$ by clamping the first inhale function $I(t_a, t_b)$ to the range $-1 \leq I_c(t_a, t_b) \leq 1$. Thus, if the first inhale function $I(t_a, t_b)$ is greater than or equal to one, the clamp 332 may output a one. Or, if the first inhale function $I(t_a, t_b)$ is less than or equal to negative one, the clamp 332 may output a zero. Or, if the first inhale function $I(t_a, t_b)$ is between negative one and one, the clamp 332 may output the value of the first inhale function $I(t_a, t_b)$.

The breathing classifier 334 may calculate the third inhale function $I_n(t_a, t_b)$ based on the value of the second inhale function $I_c(t_a, t_b)$ output by the clamp 332. If the second inhale function $I_c(t_a, t_b)$ is one, the breathing classifier 334 may output a one. Or, if the second inhale function $I_c(t_a, t_b)$ is negative one, the breather classifier 334 may output a zero. Or, if the second inhale function $I_c(t_a, t_b)$ is between negative one and one, the breathing classifier 334 may output a value between zero and one. The value of the third inhale function $I_n(t_a, t_b)$ calculated by the breathing classifier 334 may be output as the control signal 320 to the cardiac module 314.

The heart beat detector 336 of the cardiac module 314 may receive the second data signal 310 from the sensor hub 326 and may output a heart beat signal 346 to the distributor 340 and/or the heart beat interval timer 338 each time a periodic maximum representing a heart beat is detected in the second data signal 310. Optionally, detected heart beats may be discarded when a subsequent heart beat is detected within less than a predetermined fraction of an immediately preceding duration between sequential heart beats. For example, a second heart beat detected within ⅓ of the time of an immediately preceding duration may be considered erroneous and may be discarded.

The heart beat interval timer 338 may receive the heart beat signal 346 output by the heart beat detector 336 representing a sequence of detected heart beats. The heart beat interval timer 338 may output a time interval signal 348 indicating a duration of each time interval between each sequential pair of detected heart beats.

The distributor 340 may receive the heart beat signal 346 from the heart beat detector 336, the time interval signal 348 from the heart beat interval timer 338, and the control signal 320 from the breathing classifier 334. The heart beats indicated by the heart beat signal 346 and the time intervals indicated by the time interval signal 348 may be provided to the inhale accumulator pair 342, the exhale accumulator pair 344, or both, according to or weighted by the control signal 320 and consistent with the disclosure provided above.

For example, when the control signal 320 includes a value of one, the heart beat(s) indicated by the heart beat signal 346 and the time interval(s) indicated by the time interval signal 348 may be respectively provided to an inhale beat accumulator and an inhale time accumulator included in the inhale accumulator pair 342. Alternately or additionally, when the control signal 320 includes a value of zero, the heart beat(s) indicated by the heart beat signal 346 and the time interval(s) indicated by the time interval signal 348 may be respectively provided to an exhale beat accumulator and an exhale time accumulator included in the exhale accumulator pair 344. Alternately or additionally, when the control signal 320 includes a value between zero and one, a first portion $p_1$ (described above) of both the heart beat(s) indicated by the heart beat signal 346 and the time interval(s) indicated by the time interval signal 348 may be respectively provided to the inhale beat accumulator and the inhale time accumulator included in the inhale accumulator pair 342, and a second portion $p_2$ (described above) of both the heart beat(s) indicated by the heart beat signal 346 and the time interval(s) indicated by the time interval signal 348 may be respectively provided to the exhale beat accumulator and the exhale time accumulator included in the exhale accumulator pair 344.

The accumulated heart beats and time intervals from each of the inhale accumulator pair 342 and the exhale accumulator pair 344 may be provided to the stress adaptability engine 318. The stress adaptability engine 318 may then calculate the inhale average heart rate, $P_i(t)$, and the exhale average heart, $P_e(t)$, based on the accumulated heart beats and time intervals received from the inhale accumulator pair 342 and the exhale accumulator pair 344.

Accordingly, some embodiments described herein may calculate a stress adaptability of a subject, or other physiological adaptability of a subject, by extracting spectral characteristics from each of the first and second data signals and combining the spectral characteristics to determine the stress adaptability or other physiological adaptability as described above.

Figure 4:
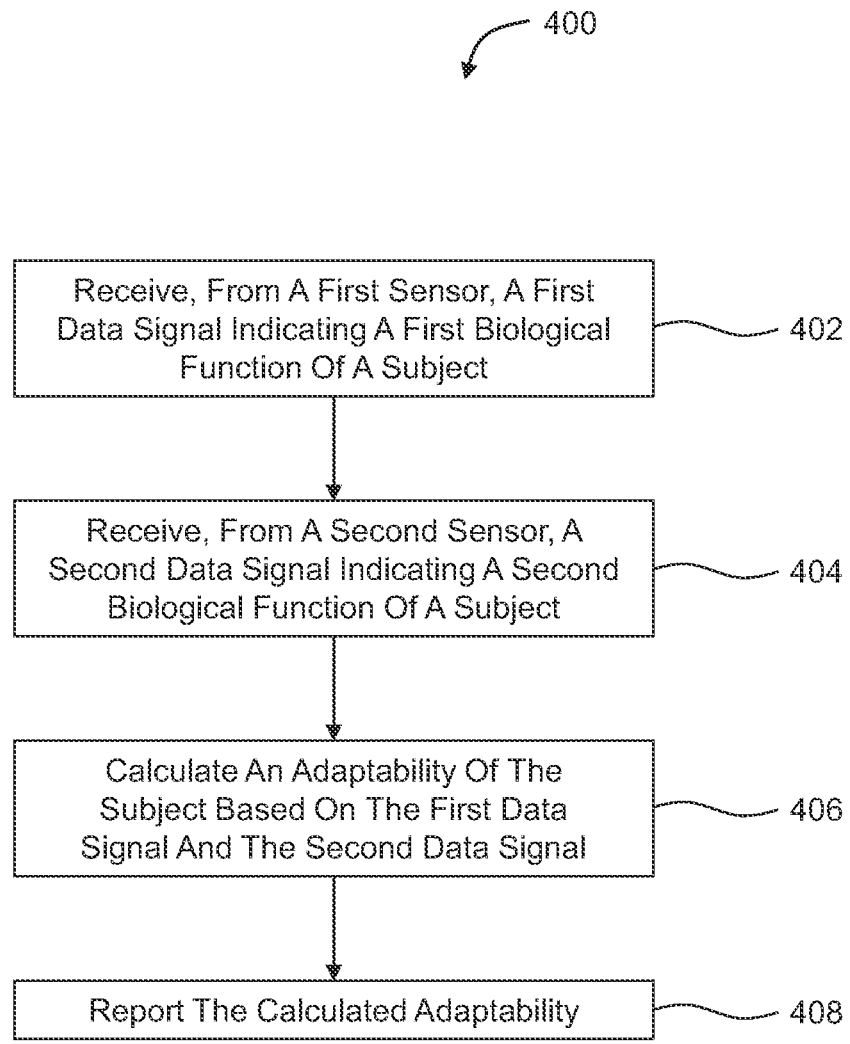
FIG. 4 is a flowchart of an example method of measuring physiological adaptability of a subject.

FIG. 4 is a flowchart of an example method 400 of measuring physiological adaptability of a subject. The method 400 and/or variations thereof may be implemented, in whole or in part, by a system, such as any of the systems 104, 300A, 300B described herein. Alternately or additionally, the method 400 and/or variations thereof may be implemented, in whole or in part, by a processor or other processing device using first and second data signals generated by first and second sensors, each indicating a corresponding biological function of a subject. Although illustrated as discrete blocks, various blocks may be divided into additional blocks, combined into fewer blocks, or eliminated, depending on the desired implementation.

The method 400 may begin at block 402 in which a first data signal indicating a first biological function of a subject may be received from a first sensor. For example, the first data signal may be received by the computing device 104A or 306—or by a processing device of the computing device 104A or 306—from the first sensor 104B or the respiratory sensor 302 described above. Optionally, the method 400 may further include, prior to receiving the first data signal, generating the first data signal at the first sensor.

In block 404, a second data signal indicating a second biological function of the subject may be received from a second sensor. For example, the second data signal may be received by the computing device 104A or 306—or by a processing device of the computing device 104A or 306—from the second sensor 104C or the cardiac sensor 304 described above. Optionally, the method 400 may further include, prior to receiving the second data signal, generating the second data signal at the second sensor.

In block 406, an adaptability of the subject may be calculated based on the first data signal and the second data signal.

In block 408, the calculated adaptability may be reported. For example, the calculated adaptability may be reported to a user such as a healthcare worker including a doctor or nurse, or to the subject.

In some embodiments, the first biological function may include a respiratory function, the second biological function may include a cardiac function, and the adaptability of the subject may include a stress adaptability of the subject as described herein.

One skilled in the art will appreciate that, for this and other processes and methods disclosed herein, the functions performed in the processes and methods may be implemented in differing order. Furthermore, the outlined steps and operations are only provided as examples, and some of the steps and operations may be optional, combined into fewer steps and operations, or expanded into additional steps and operations without detracting from the essence of the disclosed embodiments.

For example, the method 400 may further include detecting a sequence of heart beats in the second data signal, each sequential pair of detected heart beats defining a start time and an end time of an associated time interval. The sequence of heart beats may be detected by, e.g., the heart beat detector 336 of FIG. 3B. The associated time intervals may be measured by, e.g., the heart beat interval timer 338 of FIG. 3B.

In these and other embodiments, calculating a stress adaptability of the subject based on the first data signal and the second data signal may include determining time intervals when the subject is generally inhaling and time intervals when the subject is generally exhaling; determining a first average heart rate corresponding to time intervals when the subject is generally inhaling; determining a second average heart rate corresponding to time intervals when the subject is generally exhaling; and calculating a difference between the first average heart rate and the second average heart rate.

According to these and other embodiments, determining time intervals when the subject is generally inhaling and time intervals when the subject is generally exhaling may include, for each time interval, determining a difference between a first instantaneous measurement of the respiratory function and a second instantaneous measurement of the respiratory function. The first instantaneous measurement may correspond to the start time of the corresponding time interval and the second instantaneous measurement may correspond to the end time of the corresponding time interval. The difference may be divided by a threshold value, such as the threshold value $S_{de}(t_b)$ described above. If the difference divided by the threshold value is greater than or equal to one, it may be determined that the subject is inhaling during the corresponding time interval, consistent with the discussion of Equations 1-10 above. Alternately or additionally, if the difference divided by the threshold value is less than or equal to negative one, it may be determined that the subject is exhaling during the corresponding time interval, consistent with the discussion of Equations 1-10 above. Alternately or additionally, if the difference divided by the threshold value is between negative one and one, it may be determined that the corresponding time interval is a split time interval including a first portion and a second portion and that the subject is inhaling during the first portion and exhaling during the second portion, consistent with the discussion of Equations 1-10 above.

As described above with respect to, e.g., Equations 1-2, the threshold value may be based on a difference between a maximum instantaneous measurement of the respiratory function and a minimum instantaneous measurement of the respiratory function during a temporal window having a predetermined length, such as $T_w = 1000$ seconds.

Alternately or additionally, determining a first average heart rate corresponding to time intervals when the subject is generally inhaling may include, in a first beat accumulator, such as the inhale beat accumulator $A_{ib}$ described above, accumulating one heart beat for each time interval during which the subject is determined to be inhaling. In a first time accumulator, such as the inhale time accumulator $A_{id}$ described above, each time interval during which the subject is determined to be inhaling may be accumulated. For each split time interval and corresponding heart beat, a first fraction of the split time interval corresponding to the first portion of the split time interval may be accumulated in the first time accumulator and a same first fraction of the corresponding heart beat may be accumulated in the first beat accumulator. A sum of accumulated heart beats from the first beat accumulator may then be divided by a corresponding sum of accumulated time intervals from the first time accumulator to complete the determination of the first average heart rate.

Alternately or additionally, determining a second average heart rate corresponding to time intervals when the subject is generally exhaling may include, in a second beat accumulator, such as the exhale beat accumulator $A_{eb}$ described above, accumulating one heart beat for each time interval during which the subject is determined to be exhaling. In a second time accumulator, such as the exhale time accumulator $A_{ed}$ described above, each time interval during which the subject is determined to be exhaling may be accumulated. For each split time interval and corresponding heart beat, a second fraction of the split time interval corresponding to the second portion of the split time interval may be accumulated in the second time accumulator and a same second fraction of the corresponding heart beat may be accumulated in the second beat accumulator. A sum of accumulated heart beats from the second beat accumulator may then be divided by a corresponding sum of accumulated time intervals from the second time accumulator to complete the determination of the second average heart rate.

In some embodiments, each sequential pair of heart beats may include a first heart beat detected at a corresponding start time and a second heart beat detected at a corresponding end time of the associated time interval. It will be appreciated, with the benefit of the present disclosure, that the first heart beat of a given time interval may correspond to the second heat beat of an immediately preceding time interval. In these and other embodiments, detecting a sequence of heart beats in the second data signal may include calculating a duration of each associated time interval. The duration of each time interval may be compared to a duration of an immediately preceding time interval. When the duration of a given time interval is greater than a predetermined fraction, such as ⅓, of a duration of the immediately preceding time interval, the second heart beat of the given time interval may be discarded and the first heart beat may be paired with a next heart beat in the sequence of detected heart beats. Accordingly, some embodiments may include filtering or otherwise processing the second data signal to discard erroneous detected heart beats.

Figure 5:
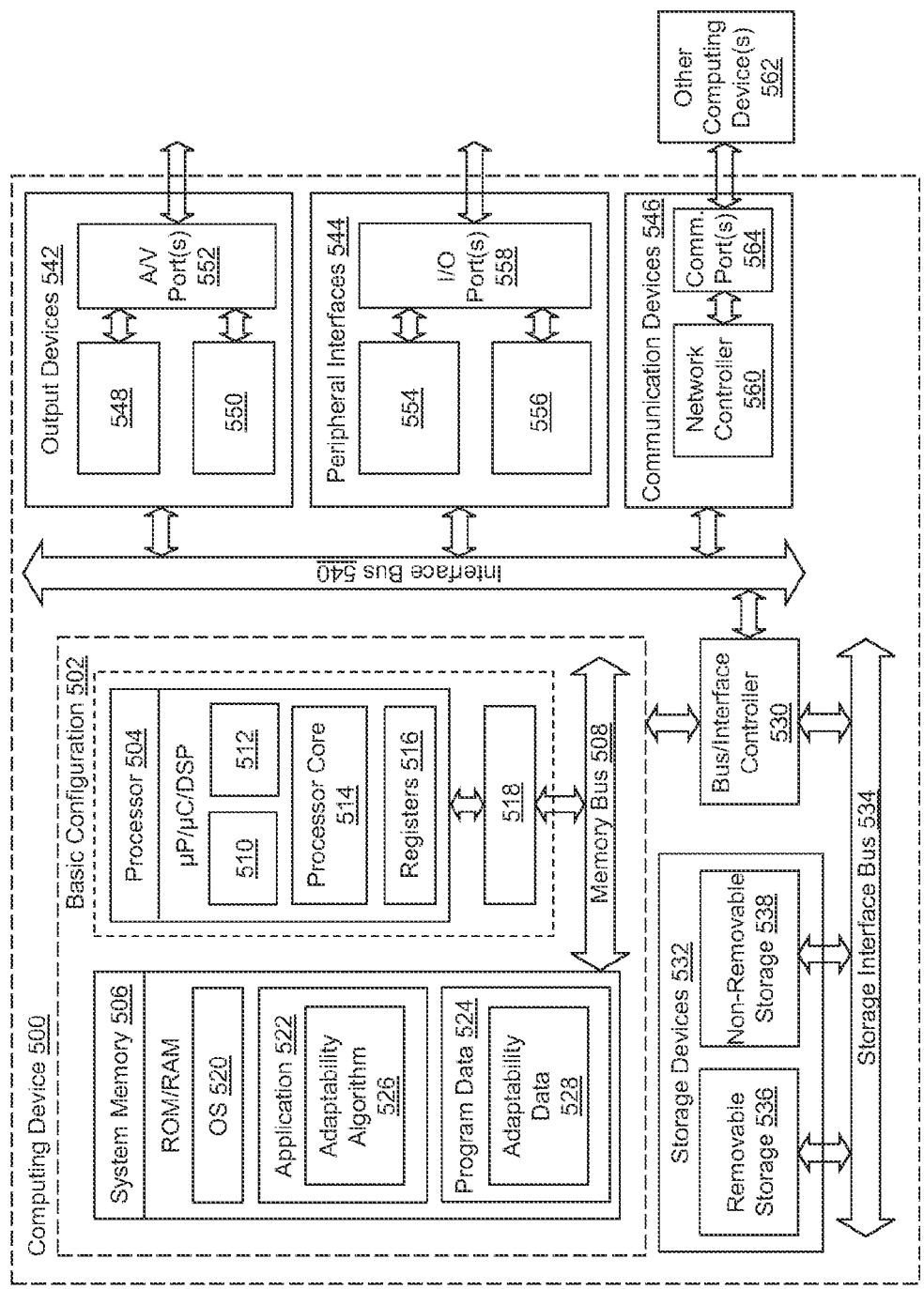
FIG. 5 is a block diagram illustrating an example computing device that is arranged for determining stress adaptability or other physiological adaptability in accordance with the present disclosure.

FIG. 5 is a block diagram illustrating an example computing device 500 that is arranged for determining stress adaptability or other physiological adaptability in accordance with the present disclosure. The computing device 500 is one example of an embodiment of the computing device 306 of FIGS. 3A-3B. In a very basic configuration 502, computing device 500 typically includes one or more processors 504 and a system memory 506. A memory bus 508 may be used for communicating between processor 504 and system memory 506.

Depending on the desired configuration, processor 504 may be of any type including but not limited to a microprocessor (μP), a microcontroller (μC), a digital signal processor (DSP), or any combination thereof. Processor 504 may include one more levels of caching, such as a level one cache 510 and a level two cache 512, a processor core 514, and registers 516. An example processor core 514 may include an arithmetic logic unit (ALU), a floating point unit (FPU), a digital signal processing core (DSP Core), or any combination thereof. An example memory controller 518 may also be used with processor 504, or in some implementations memory controller 518 may be an internal part of processor 504.

Depending on the desired configuration, system memory 506 may be of any type including but not limited to volatile memory (such as RAM), non-volatile memory (such as ROM, flash memory, etc.) or any combination thereof. System memory 506 may include an operating system 520, one or more applications 522, and program data 524. Application 522 may include an adaptability algorithm 526 that is arranged to perform the functions as described herein including those described with respect to the method 400 of FIG. 4. Program data 524 may include adaptability data 528 that may be useful for operation with the adaptability algorithm 526 as is described herein. In some embodiments, application 522 may be arranged to operate with program data 524 on operating system 520 such that measuring a physiological adaptability of a subject may be provided as described herein.

Computing device 500 may have additional features or functionality, and additional interfaces to facilitate communications between basic configuration 502 and other devices and interfaces. For example, a bus/interface controller 530 may be used to facilitate communications between basic configuration 502 and one or more data storage devices 532 via a storage interface bus 534. Data storage devices 532 may be removable storage devices 536, non-removable storage devices 538, or a combination thereof. Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 506, removable storage devices 536 and non-removable storage devices 538 are examples of computer storage media. Computer storage media includes, but is not limited to, Random Access Memory (RAM), Read Only Memory (ROM), Electronically Erasable and Programmable Read Only Memory (EEPROM), flash memory or other memory technology, Compact Disc-Read Only Memory (CD-ROM), digital versatile disks (DVD) or other optical storage, magnetic cassettes, magnetic tape, magnetic disk storage or other magnetic storage devices, or any other medium which may be used to store the desired information and which may be accessed by computing device 500. Any such computer storage media may be part of computing device 500.

Computing device 500 may also include an interface bus 540 for facilitating communication from various interface devices (e.g., output devices 542, peripheral interfaces 544, and communication devices 546) to basic configuration 502 via bus/interface controller 530. Example output devices 542 include a graphics processing unit 548 and an audio processing unit 550, which may be configured to communicate to various external devices such as a display or speakers via one or more A/V ports 552. Example peripheral interfaces 544 include a serial interface controller 554 or a parallel interface controller 556, which may be configured to communicate with external devices such as input devices (e.g., keyboard, mouse, pen, voice input device, touch input device, etc.) or other peripheral devices (e.g., printer, scanner, etc.) via one or more I/O ports 558. An example communication device 546 includes a network controller 560, which may be arranged to facilitate communications with one or more other computing devices 562 over a network communication link via one or more communication ports 564.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 500 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 500 may also be implemented as a personal computer including both laptop computer and non-laptop computer configurations.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

What is claimed is:

1. A method of measuring physiological adaptability of a subject, the method comprising:
   receiving, from a first sensor, a first data signal indicating a first biological function of the subject;
   receiving, from a second sensor, a second data signal indicating a second biological function of the subject;
   calculating a stress adaptability of the subject based on the first data signal and the second data signal, comprising:
      determining, based on the first data signal from the first sensor and the second data signal from the second sensor, a single first average heart rate corresponding to time intervals when the subject is generally inhaling;
      determining, based on the first data signal from the first sensor and the second data signal from the second sensor, a single second average heart rate corresponding to time intervals when the subject is generally exhaling; and calculating the stress adaptability based on a difference between the single first average heart rate and the single second average heart rate; and reporting the calculated stress adaptability, wherein the first biological function includes a respiratory function, the second biological function includes a cardiac function;

wherein the method further comprises detecting a sequence of heart beats in the second data signal, each sequential pair of detected heart beats in the detected sequence of heart beats defining a start time and an end time of an associated time interval; and wherein the calculating the stress adaptability of the subject based on the first data signal and the second data signal further comprises determining time intervals of the sequential pairs of detected heart beats when the subject is generally inhaling and time intervals of the sequential pairs of detected heart beats when the subject is generally exhaling.

2. The method of claim 1, wherein:

receiving the first data signal indicating the first biological function of the subject comprises receiving the first data signal indicating the first biological function of the subject that varies over time; and receiving the second data signal indicating the second biological function of the subject comprises receiving the second data signal indicating the second biological function of the subject that varies over time in dependence on a variability of the first biological function.

3. The method of claim 1, wherein receiving the first and second data signals comprises receiving the first and second data signals while the subject is moving in an uncontrolled environment.

4. The method of claim 1, wherein determining time intervals of the sequential pairs of detected heart beats when the subject is generally inhaling and time intervals of the sequential pairs of detected heart beats when the subject is generally exhaling includes, for each time interval:

determining a difference between a first instantaneous measurement of the respiratory function and a second instantaneous measurement of the respiratory function, the first instantaneous measurement corresponding to the start time and the second instantaneous measurement corresponding to the end time of the corresponding time interval;

dividing the difference by a threshold value;

when the difference divided by the threshold value is greater than or equal to one, determining that the subject is inhaling during the corresponding time interval;

when the difference divided by the threshold value is less than or equal to negative one, determining that the subject is exhaling during the corresponding time interval; and when the difference divided by the threshold value is between negative one and one, determining that the corresponding time interval is a split time interval including a first portion and a second portion and that the subject is inhaling during the first portion and exhaling during the second portion.

5. The method of claim 4, wherein;

the threshold value is based on a difference between a maximum instantaneous measurement of the respiratory function and a minimum instantaneous measurement of the respiratory function during a temporal window having a predetermined length;

determining a first average heart rate corresponding to time intervals when the subject is generally inhaling includes:

in a first beat accumulator, accumulating one heart beat for each time interval during which the subject is determined to be inhaling;

in a first time accumulator, accumulating each time interval during which the subject is determined to be inhaling;

for each split time interval and corresponding heart beat:

in the first time accumulator, accumulating a first fraction of the split time interval corresponding to the first portion of the split time interval; and in the first beat accumulator, accumulating a same first fraction of the corresponding heart beat; and dividing a sum of accumulated heart beats from the first beat accumulator by a corresponding sum of accumulated time intervals from the first time accumulator; and determining a second average heart rate corresponding to time intervals when the subject is generally exhaling includes:

in a second beat accumulator, accumulating one heart beat for each time interval during which the subject is determined to be exhaling;

in a second time accumulator, accumulating each time interval during which the subject is determined to be exhaling;

for each split time interval and corresponding heart beat:

in the second time accumulator, accumulating a second fraction of the split time interval corresponding to the second portion of the split time interval; and in the second beat accumulator, accumulating a same second fraction of the corresponding heart beat; and dividing a sum of accumulated heart beats from the second beat accumulator by a corresponding sum of accumulated time intervals from the second time accumulator.

6. The method of claim 1, wherein:

each sequential pair of detected heart beats includes a first heart beat detected at a corresponding start time and a second heart beat detected at a corresponding end time of the associated time interval;

the first heart beat of a given time interval corresponds to the second heart beat of an immediately preceding time interval; and detecting a sequence of heart beats in the second data signal includes:

calculating a duration of each of the associated time intervals;

comparing a duration of each time interval to a duration of an immediately preceding time interval; and when the duration of the given time interval is less than a predetermined fraction of the duration of the immediately preceding time interval, discarding the second heart beat of the given time interval and pairing the first heart beat with a next heart beat in the sequence of detected heart beats.

7. A system for measuring physiological adaptability of a subject, the system comprising:

a first sensor configured to generate a first data signal indicating a first biological function of the subject, wherein the first biological function includes a respiratory function;

a second sensor configured to generate a second data signal indicating a second biological function of the subject, wherein the second biological function includes a cardiac function; and a computing device communicatively coupled to the first sensor and the second sensor, the computing device configured to:
receive the first data signal and the second data signal;
calculate a stress adaptability of the subject based on the first data signal and the second data signal, comprising:
determining, based on the first data signal from the first sensor and the second data signal from the second sensor, a single first average heart rate corresponding to time intervals when the subject is generally inhaling;
determining, based on the first data signal from the first sensor and the second data signal from the second sensor, a single second average heart rate corresponding to time intervals when the subject is generally exhaling; and
calculating the stress adaptability based on a difference between the single first average heart rate and the single second average heart rate; and
report the calculated stress adaptability to a user via an output device,
wherein the computing device is further configured to detect a sequence of heart beats in the second data signal, each sequential pair of detected heart beats in the detected sequence of heart beats defining a start time and an end time of an associated time interval;
wherein calculation by the computing device of the stress adaptability of the subject based on the first data signal and the second data signal further comprises determining time intervals of the sequential pairs of detected heart beats when the subject is generally inhaling and time intervals of the sequential pairs of detected heart beats when the subject is generally exhaling.

8. The system of claim 7, wherein the first sensor comprises a respiratory inductance plethysmograph (RIP), a blood oxygen level sensor, or a breath sensor.

9. The system of claim 7, wherein the second sensor comprises a heart rate monitor, an electrocardiography (ECG) device, or a Holter monitor.

10. The system of claim 7, further comprising a battery configured to power the system such that the system is mobile.

11. The system of claim 7, wherein the first sensor comprises a respiratory sensor, the second sensor comprises a cardiac sensor, and the computing device comprises:
a sensor hub communicatively coupled to the respiratory sensor and the cardiac sensor;
a respiratory module communicatively coupled to the sensor hub;
a cardiac module communicatively coupled to the sensor hub and to the respiratory module;
a stress adaptability analysis engine communicatively coupled to the cardiac module; and
the output device communicatively coupled to the stress adaptability analysis engine.

12. The system of claim 11, wherein:
the sensor hub is configured to receive and temporally synchronize the first data signal and the second data signal;
the respiratory module is configured to determine the time intervals of the sequential pairs of detected heart beats when the subject is generally inhaling and the time intervals of the sequential pairs of detected heart beats when the subject is generally exhaling, the respiratory module including:

a smoothing filter;
a numerical differentiator communicatively coupled to the digital smoothing filter;
a clamp coupled to the numerical differentiator; and
a breathing classifier communicatively coupled to the clamp;
the cardiac module is configured to collect heart beat and time interval data associated with time intervals when the subject is generally inhaling and time intervals when the subject is generally exhaling, the cardiac module including:
a heart beat detector;
a heart beat interval timer communicatively coupled to the heart beat detector;
a distributor communicatively coupled to the heart beat detector and the heart beat interval timer;
an inhale accumulator pair communicatively coupled to the distributor; and
an exhale accumulator pair communicatively coupled to the distributor;
the stress adaptability analysis engine is configured to:
determine the single first average heart rate corresponding to time intervals when the subject is generally inhaling;
determine the single second average heart rate corresponding to time intervals when the subject is generally exhaling; and
calculate the difference between the single first average heart rate and the single second average heart rate as the calculated stress adaptability; and
the output device comprises a display device.

13. A processor configured to execute computer instructions to cause a computing system to perform operations for measuring physiological adaptability of a subject, the operations comprising:
receiving, from a first sensor, a first data signal indicating a first biological function of the subject;
receiving, from a second sensor, a second data signal indicating a second biological function of the subject;
calculating a stress adaptability of the subject based on the first data signal and the second data signal, comprising:
determining, based on the first data signal from the first sensor and the second data signal from the second sensor, a single first average heart rate corresponding to time intervals when the subject is generally inhaling;
determining, based on the first data signal from the first sensor and the second data signal from the second sensor, a single second average heart rate corresponding to time intervals when the subject is generally exhaling; and
calculating the stress adaptability based on a difference between the single first average heart rate and the single second average heart rate; and
reporting the calculated stress adaptability,
wherein the first biological function includes a respiratory function, the second biological function includes a cardiac function;
wherein the method further comprises detecting a sequence of heart beats in the second data signal, each sequential pair of detected heart beats in the detected sequence of heart beats defining a start time and an end time of an associated time interval; and
wherein the calculating the stress adaptability of the subject based on the first data signal and the second data signal further comprises determining time intervals of the sequential pairs of detected heart beats when the subject is generally inhaling and time intervals of the sequential pairs of detected heart beats when the subject is generally exhaling.

14. The processor of claim 13, wherein the calculated stress adaptability of the subject comprises a calculated respiratory sinus arrhythmia (RSA) of the subject.

15. The processor of claim 13, wherein the calculated stress adaptability comprises a constant number.

16. The processor of claim 13, wherein the calculating the stress adaptability of the subject based on the first data signal and the second data signal further comprises extracting spectral characteristics from each of the first data signal and the second data signal and combining the spectral characteristics to determine the adaptability.

17. The processor of claim 13, wherein the operations further include:
- temporally synchronizing the first data signal and the second data signal; and
- digitally filtering the first data signal to smooth the first data signal.

* * * * *